United States Patent [19]

Cabrera et al.

[11] 4,421,108

[45] Dec. 20, 1983

[54] SURGICAL RETRACTOR HOLDER

[75] Inventors: Rene J. Cabrera, Brockton; George W. Guay, North Scituate, both of Mass.; John R. Bookwalter, Brattleboro, Vt.

[73] Assignee: Codman & Shurtleff, Inc., Randolph, Mass.

[21] Appl. No.: 286,908

[22] Filed: Jul. 27, 1981

[51] Int. Cl.[3] .............. A61B 17/02

[52] U.S. Cl. .............. 128/20; 128/303 B; 248/226.5

[58] Field of Search .............. 128/20, 303 B; 248/221.3, 299, 226.5, 560

[56] References Cited

U.S. PATENT DOCUMENTS

| | | | |
|---|---|---|---|
| D. 148,099 | 12/1947 | Tanchuck | 248/226.5 X |
| 2,456,553 | 12/1948 | Churchill | 248/226.5 X |
| 2,752,709 | 7/1956 | Gough | 248/226.5 X |
| 3,749,088 | 7/1973 | Gauthier | 128/20 |
| 4,112,550 | 9/1978 | DeWitt et al. | 248/226.5 X |
| 4,254,763 | 3/1981 | McCready et al. | 128/20 |

*Primary Examiner*—Kyle L. Howell
*Assistant Examiner*—Christine A. Fukushima
*Attorney, Agent, or Firm*—Donal B. Tobin

[57] ABSTRACT

A quick-release ratcheting holder for a surgical retractor which includes a spring detent to keep the holder from coming off the ring member when the retractor is relaxed.

2 Claims, 3 Drawing Figures

81 80 72 78 79 82 94 92 96 90 98

10
12
14
15
16
18
19
70
72
74
75
76
78
79
80
81
82
90
92
94
96
98
P

SURGICAL RETRACTOR HOLDER

BACKGROUND OF THE INVENTION

The present invention relates to a surgical retractor holder, and more particularly, to a spring detent to keep the holder from coming off its support ring when the retractor is released.

In surgical operations on the chest or abdomen, it is customary to employ a retraction apparatus. Most, if not all, versions of the retraction apparatus are attached directly to the operating room table by means of affixation to a rail which is provided along each side of the table. By connection to one or both rails, the retraction apparatus generally provides a framework extending over the region of the patient in which the operation is to be performed. One or more retractor blades are attached to the apparatus framework, which may be a ring, and these blades are positioned in the incision and serve to hold back tissue, organs, and the like so that the surgeon may operate on the intended area. These retractors, known as self-retaining surgical retractors, contribute to the efficiency of the surgeon, and are generally sufficiently adjustable to be useful in a variety of such surgical operations. Typical variations of this type of retractor are found in U.S. Pat. Nos. 3,572,236 2,594,086 and 2,586,488. Although the known and available self-retaining surgical retractors offer many advantages in the operating room, some deficiencies are evident as well.

Retractor blades usually include a long handle which engages a holder. The holder mounts on the apparatus framework or ring. Many holders are attached to the ring by means of a set screw or other means. Moving the holder requires unscrewing the set screw, moving the retractor and then tightening the screw. It would be desirable to have a holder which eliminated the loosening and tightening of a set screw but at the same time was securely fastened to the ring.

SUMMARY OF THE INVENTION

Surgical retractor assemblies include a support post which clamps to the operating table. An extension rod is adjustably connected to the post and is adapted to extend in a direction generally over a patient on the operating table. The extension rod clamps to a generally oval-shaped ring. At least one retractor blade is connected to the ring by a holder.

Preferably, a plurality of retractor blades are mounted on the ring member by separate holders, with each blade being adjustable both in its position along the ring member and in a general radial direction toward the open center of the ring member.

Each holder includes a quick-release ratchet mechanism which attaches the retractor blades to the ring member. The holder has an open slot for receiving the ring and a spring detent whose end closest to the ring center is enlarged to snap around the ring and keep the holder engaged in the ring when the retraction is relaxed. The spring detent only loosely retains the holder so that the holder may be easily moved along the ring. No wing nuts or screws are required in this invention in order to make the attachment of retractor blade to the ring member.

DETAILED DESCRIPTION

Figures 1, 2, 3:
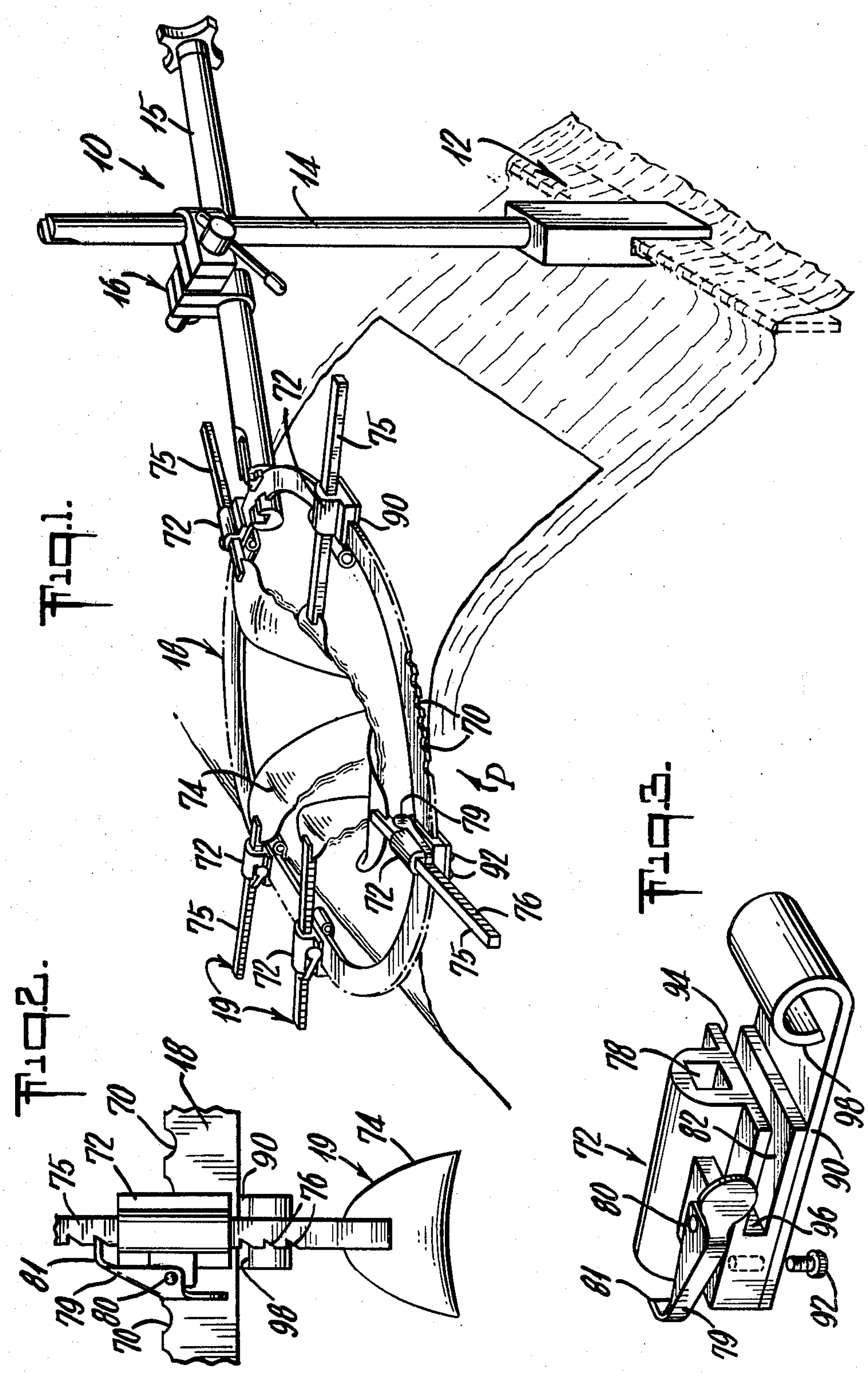
FIG. 1 is a perspective view illustrating the preferred surgical retractor assembly attached to a surgical operating table and ready for use in a surgical operation on a patient.
FIG. 2 is a top plan view of one retractor blade attached to the ring member, shown in partial view; and, FIG. 3 is an enlarged perspective view of the preferred pawl mechanism for attaching the retractor blade to the ring member.

While this invention is satisfied by embodiments in many different forms, there is shown in the drawings, and will herein be described in detail, a preferred embodiment of the invention with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated a self-retaining surgical retractor assembly 10 attached to a surgical operating room table 12 and in a position as it would appear during an operation on a simulated patient P. The main components comprising this surgical retractor are an elongated support post 14, an elongate extension rod 15 which is connected to support post 14 by a coupling device 16, a substantially flat, oval-shaped ring member 18 adjustably affixed to extension rod 15 and a plurality of retractor blades 19 adjustably mounted on ring member 18.

In FIGS. 2 and 3, one retractor blade 19 is shown mounted on ring member 18 with its quick-release pawl attachment mechanism with body section 72. The retractor blade includes the blade portion 74 which is inserted into an incision for restraining tissue, organs and the like during the surgical procedure. A handle 75 extends from blade portion 74 and, in the embodiment being described, preferably has a square or rectangular cross-section. Along one surface of handle 75 is a plurality of spaced ratchet teeth 76 which are spaced to provide small incremental adjustments of the handle. Handle 75 is inserted through a compatible opening bore 78 extending through body section 72, as seen in FIG. 3. Teeth 76 on the handle face a spring-loaded pawl 79 which is connected by a pivot pin 80 to the pawl mechanism. The leading edge 81 of pawl 79 mates with teeth 76 and thereby locks the handle in a fixed position. The mechanism is slid onto ring member 18 by means of a slot 82 through the body 95 of the pawl mechanism. Slot 82 is open to the opposite surface from that surface which leading edge 81 of the pawl extends. Although not seen in FIG. 3, slot 82 may incorporate a dowel or other pin with a smooth radius to matingly fit into an indentation 70 on ring member 18, to hold the pawl mechanism securely onto the ring member. By referring to FIG. 2, it can be seen that body section 72 holds retractor blade 19 so that the handle extends in a generally radial direction and is thus adjustable in the radial direction by means of pawl 79 and ratchet teeth 76. It is appreciated that the pawl mechanism requires no screws, wing nuts, or other fixation devices inasmuch as the inwardly directed radial force transmitted from blade portion 74 during use of the retractor tends to maintain the pawl mechanism in position on ring member 18. This type of pawl mechanism mounting with the various retractors can be seen by referring to FIG. 1, which shows retractor blades 19 in a position as they may appear during a surgical operation on a patient P.

It can be seen that each retractor may be adjustably positioned to any desirable annular position on ring member 18; also, each retractor blade may be adjusted in a generally radial direction toward or away from the open center of the ring member. A spring detent 90 is attached to the bottom of body section 72 by means of screws 92. The front end of detent 90 curls up to a height slightly higher than the top surface 94 of slot 82. The radial distance between the inside surface 96 of slot 82 and the confronting surface 98 of spring detent 90 is somewhat longer than the width of annular ring 18 so that the pawl mechanism will stay loosely engaged on ring 18 when the retraction is relaxed without impeding the motion of the holder of along ring 18.

We claim:

1. In a surgical retractor blade holder having a quick-release pawl attachment mechanism for attaching a retractor blade to a supporting structure, said retractor blade having a retractor blade handle having ratchet teeth disposed along at least one surface thereof, said quick-release pawl attachment mechanism having:

a body section having a bottom surface a bore through said body section for receiving said retractor blade handle, said bore having an interior surface;

a pawl pivotably mounted to said body section, said pawl having a leading edge for engaging cooperating ratchet teeth on said retractor blade handle; and an open slot in said body section for engaging a supporting structure, said slot having an inside surface and a top and a bottom surface, none of said slot surfaces being in common with said bore surfaces;

the improvement comprising:

a spring detent attached to said body section bottom surface, aligned with said slot in said body section and extending beyond the end of said bottom surface;

the free end of said spring detent including a raised portion and providing a confronting surface aligned with said open slot, the top of said raised portion extending above the top surface of said slot but not obstructing access of a blade retractor handle to said bore through said body section;

the confronting surface of said raised portion spaced apart from the inside surface of said slot a distance greater than the width of said supporting structure;

whereby said retractor blade holder may be placed on said supporting structure by displacing said spring detent and sliding said slot onto said supporting structure until said spring detent springs back into position on the opposite side of the supporting structure to loosely hold said holder on said supporting structure even when said retractor is in the relaxed position.

2. The apparatus of claim 1 wherein said raised portion of said spring detent includes an arcuate portion extending in a continuous curve from the remainder of said spring detent.

* * * * *